US 6,737,382 B1

(12) United States Patent
Iwataki et al.

(10) Patent No.: US 6,737,382 B1
(45) Date of Patent: May 18, 2004

(54) INSECTICIDAL AMINOTHIAZOLE DERIVATIVES

(75) Inventors: Isao Iwataki, Gainesville, FL (US); Takao Iwasa, Kanagawa (JP); Renpei Hatano, Kanagawa (JP); Elizabeth Laura Moyano, Cordova (AR)

(73) Assignee: Nippon Soda Co. Ltd., Tokyo (JP)

( * ) Notice: Subject to any disclaimer, the term of this patent is extended or adjusted under 35 U.S.C. 154(b) by 39 days.

(21) Appl. No.: 10/279,053

(22) Filed: Oct. 23, 2002

(51) Int. Cl.$^7$ .................. A01N 43/78; C07D 277/32
(52) U.S. Cl. .................. 504/252; 504/266; 546/270.7; 548/195; 548/198
(58) Field of Search .................. 548/195, 198; 546/270.7; 504/252, 266

(56) References Cited

U.S. PATENT DOCUMENTS

| | | |
|---|---|---|
| 4,199,506 A | 4/1980 | Howe et al. |
| 4,284,426 A | 8/1981 | Howe et al. |
| 4,371,389 A | 2/1983 | Howe et al. |
| 4,437,875 A | 3/1984 | Howe et al. |
| 4,437,876 A | 3/1984 | Howe et al. |

FOREIGN PATENT DOCUMENTS

| | | | |
|---|---|---|---|
| GB | 2 331 748 A | | 2/1999 |
| JP | 1019527 A | * | 7/1998 |

OTHER PUBLICATIONS

An English translation JP 10195072, 1998.*
Wilkes et al., CA 118:2434, 1993.*
Wilkes et al., Journal of Agricultural and Food Chemistry (1991), 39(9), pp. 1652–1657.*
CA Registry No. 382171–18–8, entry date in the Chemical Abstracts Service Registry database—Jan. 11, 2002.*
CA Registry No. 382170–61–8, entry date in the Chemical Abstracts Service Registry database—Jan. 11, 2002.*
TimTec Stock A (Catalog published Oct. 4, 2002).*
Interchim Intermediates (Catalog published Jul. 9, 2002).*
Ambinter: Exploratory Library (Catalog published Jan. 21, 2002).*
Chemical Block Stock Library (Catalog published Aug. 1, 2002).*
CA Registry No. 328006–15–1, entry date in the Chemical Abstracts Service Registry database—2001.*
CA Registry No. 256414–67–2, entry date in the Chemical Abstracts Service Registry database—Feb. 21, 2000.*
CA Registry No. 256414–66–1, entry date in the Chemical Abstracts Service Registry database—Feb. 21, 2000.*
CA Registry No. 256414–64–9, entry date in the Chemical Abstracts Service Registry database—Feb. 21, 2000.*
CA Registry No. 339219–89–5, entry date in the Chemical Abstracts Service Registry database—Jun. 1, 2001.*
CA Registry No. 339208–75–2, entry date in the Chemical Abstracts Service Registry database—Jun. 1, 2001.*
CA Registry No. 311793–94–9, entry date in the Chemical Abstracts Service Registry database—Jan. 28, 2000.*
CA Registry No. 296791–42–9, entry date in the Chemical Abstracts Service Registry database—Oct. 18, 2000.*
CA Registry No. 296791–40–7, entry date in the Chemical Abstracts Service Registry database—Oct. 18, 2000.*
CA Registry No. 256414–68–3, entry date in the Chemical Abstracts Service Registry database—Feb. 21, 2000.*
CA Registry No. 256414–60–0, entry date in the Chemical Abstracts Service Registry database—Feb. 21, 2000.*
CA Registry No. 256414–61–6, entry date in the Chemical Abstracts Service Registry database—Feb. 21, 2000.*
ChemDiv, Inc. Product Library (Catalog published Apr. 26, 2001).*
Screening Collection (Catalog published Mar. 28, 2000).*
Compounds For Screening (Catalog published Jul. 1, 2001).*

* cited by examiner

Primary Examiner—Laura L. Stockton
(74) Attorney, Agent, or Firm—Dennis G. LaPointe; Mason Law, P.A.

(57) ABSTRACT

Insecticidal aminothiazole derivatives and the use as an insecticide and acaricide of the compounds of formula (1):

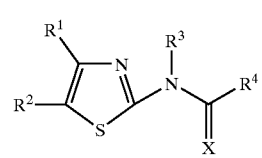

(1)

wherein $R^1$ is cyano or fluoroalkyl, $R^2$ is halogen, SCN or aryl, $R^3$ is H, $C_1$–$C_6$ alkyl, $SO_2R^5$ or $C(O)R^6$, $R^4$ and $R^6$ are, independently, aryl, phenylalkyl, alkyl, cycloalkyl groups, being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy; said aryl, phenylalkyl groups may additionally be fused to a cycloalkyl ring, $R^5$ is $C_1$–$C_6$ alkyl, haloalkyl, X is O, S, $NR^7$, $R^7$ is alkyl, cycloalkyl, alkoxy, alkenylalkyloxy, alkynylalkyloxy, alkoxycarbonylalkyloxy.

6 Claims, No Drawings

INSECTICIDAL AMINOTHIAZOLE DERIVATIVES

BACKGROUND OF THE INVENTION

1. Field of the Invention

The present invention relates to novel thiazole derivatives, which have insecticidal and acaricidal activity. The preparation and use, in agriculture and horticulture, of agrochemical compositions containing these novel insecticidal thiazoles are also disclosed.

2. Description of the Related Art

It is known in the art that certain thiazole derivatives such as those disclosed in U.S. Pat. Nos. 4,199,506, 4,284,426, 4,371,389, 4,437,875, 4,437,876 have herbicide antidote properties and in Japan Kokai Koho 06-25199 have fungicidal properties. Furthermore, it is known in the art that UK patent application GB 2331748 discloses 5-cyano or thiocarbamoyl thiazole derivatives and their use as insecticides, acaricides or nematocides. The present invention concerns the novel thiazole derivatives which have excellent insecticidal and acaricidal activity.

SUMMARY OF THE INVENTION

In accordance with the present invention, thiazole derivatives are provided having the formula (1):

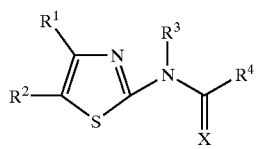

(1)

wherein
- $R^1$ is cyano or fluoroalkyl,
- $R^2$ is halogen, SCN or aryl,
- $R^3$ is H, $C_1$–$C_6$ alkyl, $SO_2R^5$ or $C(O)R^6$,
- $R^4$ and $R^6$ are, independently, aryl, phenylalkyl, alkyl, cycloalkyl groups, being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy; said aryl, phenylalkyl groups may additionally be fused to a cycloalkyl ring,
- $R^5$ is $C_1$–$C_6$ alkyl, haloalkyl,
- X is O, S, $NR^7$,
- $R^7$ is alkyl, cycloalkyl, alkoxy, alkenylalkyloxy, alkynylalkyloxy, alkoxycarbonylalkyloxy.

The present invention is directed to agrochemical compositions comprising as an active ingredient at least one of the novel thiazole derivatives of the present invention, as well as to the use of these active ingredients or compositions for pest control, and, in particular as insecticides and acaricides useful in agriculture and horticulture.

For a better understanding of the present invention, reference is made to the following description and its scope will be pointed out in the appended claims.

DETAILED DESCRIPTION OF THE INVENTION

For purposes of the present invention the general terms used hereinabove and hereinbelow have the following meanings, unless otherwise defined:

Alkyl groups are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl, or 3-hexyl. Cycloalkyl groups are generally cyclopropyl, cyclobutyl, cyclopentyl, cyclohexyl. Halogen and halo substituents will be understood generally as meaning fluoro, chloro, bromo, iodo, chloro, bromo, or iodo are preferred meanings in this invention. Haloalkyl can contain identical or different halogenatoms, typically fluoromethyl, difluoromethyl, difluorochlorormethyl, trifluoromethyl, chloromethyl, trichloromethyl Fluoroalkyl is generally fluoromethyl, difluoromethyl, trifluoromethyl, pentafluoroethyl, n-heptafluoroprpyl, n-nonafluorobutyl, n-undecafluoropentyl, n-tridecafluorohexyl and preferably trifluoromethyl and pentafluoroethyl.

Alkoxy is typically methoxy, ethoxy, propyloxy, isopropyloxy, n-butyloxy, isobutyloxy, sec-butyloxy, and tert-butyloxy, methoxy and ethoxy are preferred.

Aryl is typically substituted phenyl or naphthyl, furyl, thienyl, six-membered heteroaromatic ring system such as pyridinyl, pyrimidinyl, pyridazinyl, pyrazinyl, triazinyl (1,2, 3-, 1,2,4- and 1,3,5-), quinolinyl, isoquinolinyl, cinnolinyl, quinazolinyl, quinoxalinyl, indolinyl, isoindolinyl, five membered heteroaromatic ring such as thiazolyl, isothiazolyl, oxazolyl, isoxazolyl, pyrazolyl, thiadiazolyl oxadiazolyl, pyrollyl, imidazolyl, triazolyl (1,2,3- and 1,2, 4-), tetrazolyl, fused five membered rings such as benzofuranyl, benzothienyl, benzimidazolinyl; being optionally substituted by one or more of halogen, cyano, alkyl, alkenyl, alkynyl, haloalkyl, alkoxy, nitro, alkoxycarbonyl, alkylcarbonyloxy, alkylenedioxy, alkylcarbonyl, amino, alkylamino, haloalkoxy, alkylthio, alkylsulfonyl, haloalkenyl, alkoxycarbonylalkyl or alkoxycarbonylalkoxy.

Alkenyl and alkynyl groups preferably contain from 2 to 6, more preferably from 2 to 4, carbon atoms. They can be in the form of straight or branched chains, and, where appropriate, the alkenyl groups can be of either (E)- or (Z)-configuration. Examples are vinyl, allyl, propargyl.

The alkylenedioxy groups are optionally substituted with halogene (especially fluorine) and are such as methlenedioxy or difluoromethylenedioxy. Alkoxyalkyl is $C_1$–$C_4$ alkoxy($C_1$–$C_4$)alkyl such as methoxymethyl or ethoxymethyl.

The present invention provides the use as insecticides or acaricides of thiazole derivatives having the following formula (1):

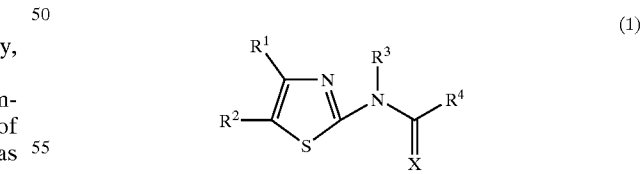

(1)

wherein $R^1$ is cyano or fluoroalkyl (especially $C_1$–$C_4$ fluoroalkyl), $R^2$ is halogen, SCN or aryl (especially phenyl, naphthyl, pyridinyl; being optionally substituted by one or more of halogen, alkyl, haloalkyl, alkoxy, nitro, alkylthio, or alkylsulfonyl), $R^3$ is H, $C_1$–$C_6$ alkyl, $SO_2R^5$ or $C(O)R^6$, $R^4$ and $R^6$ are, independently, aryl (especially phenyl, naphthyl, pyridinyl, pyrimidinyl, thienyl, furyl, thiazolyl, isothiazolyl, pyrazolyl, oxazolyl, isoxazolyl, thiadiazolyl (1,2,4, and 1,3, 4), oxadiazolyl (1,2,4- and 1,3,4); being optionally substituted by one or more of halogen, cyano, alkyl haloalkyl, alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is O, S, $NR^7$, $R^7$ is alkyl (especially $C_1$–$C_6$ alkyl), cycloalkyl (especially $C_3$–$C_6$ cycloalkyl), alkoxy (especially $C_1$–$C_6$ alkoxy), alkenylalkyloxy (especially ($C_2$–$C_6$)alkenyl($C_1$–$C_6$)alkyloxy), alkynylalkyloxy (especially ($C_2$–$C_6$)alkynyl($C_1$–$C_6$) alkyloxy), alkoxycarbonylalkyloxy (especially ($C_1$–$C_6$) alkoxycarbonyl($C_1$–$C_6$)alkyloxy).

Examples of specific compounds of formula (1) which are of use as insecticides and acaricides include the compounds listed in Table 1 at the end of this disclosure.

A compound of formula (1) wherein $R^2$ is halogen and X is oxygen can be prepared by reacting a compound of formula (2):

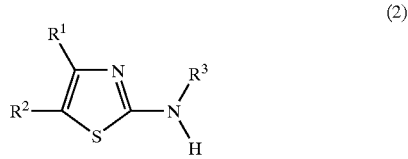

(2)

with a compound $R^4C(O)Cl$ in the presence of an organic base such as pyridine and triethylamine, or inorganic base such as potassium carbonate and sodium hydride.

A compound of formula (1) wherein $R^2$ is halogen and X is sulfur can be prepared by reacting a compound of formula (1) wherein X is oxygen with phosphorous pentasulfide in a high boiling solvent such as pyridine, picoline, lutidine, or xylene, sulfolane or by reacting a compound of formula (3):

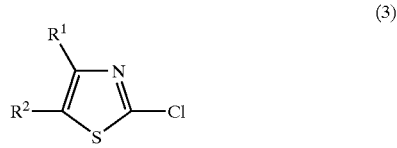

(3)

with a substituted thioamide $R^4C(S)NHR^3$ in the presence of a base such as sodium hydride or sodium hydroxide.

Surprisingly, it has now been found that the novel compounds of formula (1) have, for practical purposes, a very advantageous spectrum of activities for protecting plants against insect and acarine pests, include such as Coleoptera, Diabrotica, Diptera, Homoptera and Lepidoptera, Heteroptera, Thysanoptera, Orthoptera and Acarina. The pests include those pests associated with agriculture, horticulture and animal husbandry, forestry, the storage of products of vegetable origin, such as fruit, grain, and timber, and also those pests associated with the transmission of diseases of man and animals. Examples of insect and acarine pest species which may be controlled by the compounds of formula (1) include: *Pieris brassicae* (white butterfly), *Pseudaletia separata* (rice armyworm), *Heliothis virescens* (tobacco budworm), Trialeurodes spp. (white flies), *Aedes aegypti* (mosquito), Agrotis spp. (cutworms), *Blatta orientalis* (cockroach), Anopheles spp. (mosquitos), *Chilo partellus* (maize stem borer), Culex spp. ((mosquitos), *Dysdercus fasciatus* (capsid), *Musca domestica* (housefly), *Plutella xylostella* (diamond back moth), Aonidiella spp. (scale insects), *Bemisia tabaci* (sweetpotato white fly), *Blattella germanica* (German cockroach), *Myzus persicae* (green peach aphid), *Aphis gossypii* (cotton aphid), *Aphis fabae* (bean aphid), *Periplaneta americana* (American cockroach), *Phaedon cochleariae* (mustard beetle), *Spodoptera littoralis* (cotton leafworm), *Chortiocetes terminifera* (locust), Diabrotica spp. (rootworms), *Nilaparvata lugens* (brown rice planthopper), *Nephotettix cincticeps* (green rice leafhopper), *Tetranychus cinnabarinus* (carmine spider mite), *Panonychus ulmi* (European red mite), *Phyllocoptruta oleivora* (citrus rust mite), *Panonychus citri* (citrus red mite), *Tetranychus urticae* (two-spotted spider mite), *Polyphagotarsonemus latus* (brode mite) and Brevipalpus spp. (mites).

Compounds of the formula (1) are normally used in the form of compositions and can be applied to the crop and/or plant to be treated, simultaneously with or in succession with other compounds such as fertilizers, micronutrient donors or other preparations which influence the growth of plants. The thiazole derivatives of formula (1) can also be selectively combined with herbicides, as well as, other insecticides, fungicides, bactericides, nematocides, molluscicides or mixtures of several of these preparations and, if desired together with further carriers, surfactants or application promoting adjuvants employed in the art of formulation. In some cases, by mixing of the thiazole derivatives of formula (1) with other insecticides results synergistic insecticidal activity.

When applying the compound of the present invention in a practical way, the compound may be applied in a form as it is without adding other components. When the compound of the present invention is applied for plant protection purpose, the compound can be prepared into general types of formulations for plant protection use, such as wettable powder, granules, dust, emulsifiable concentrate, water soluble powder, suspension concentrate, flowable liquid, and so on.

In case the compound of the present invention is prepared into a solid type formulation, appropriate additives and carriers may be incorporated with the compound. Examples of the additive and the carrier include phytogenic powders, such as soybean powder and flour, mineral fine powders, such as diatomaceous earth, apatite, gypsum, talc, bentonite, pyrophyllite and clay, and organic and inorganic compounds, such as sodium benzoate, urea and Glauber's salt. In case the compound of the present invention is prepared into a liquid type formulation, an appropriate solvent is used for dissolving or dispersing the compound in the liquid type formulation. Examples of the solvent used for the liquid formulation include petroleum fractions, such as kerosine, xylene and solvent naphtha, cyclohexane, cyclohexanone, dimethylformamide, dimethylsulfoxide, alcohol, acetone, methyl isobutyl ketone, mineral oils, vegetable oils and water.

In addition, in order to provide uniformity and stability to the compound in the prepared formulations, it is possible to add surface active agents into each formulation upon necessity. There is no limitation for the surface active agent, and examples of the surface active agent that can be added to the above-mentioned formulations include nonionic surface active agents, such as polyoxyethylene-added alkyl ether, polyoxyethylene-added higher fatty acid ester, polyoxyethylene-added sorbitan higher fatty acid ester and polyoxyethylene-added tristyryl phenyl ether, a sulfate ester of polyoxyethylene-added alkyl phenyl ether, an alkyl benzene sulfonate, a polycarbonate, a lignin sulfonate, a formaldehyde condensate of alkyl naphthalene sulfonate, and a copolymer of isobutylene and maleic anhydride.

In general, the content of an active ingredient in each of the formulations recited above is preferably in a range of from 0.01 to 90% by weight, and more preferably from 0.05 to 85% by weight based on the total weight of the formulation. Each of the prepared formulations, such as wettable powder, emulsifiable concentrate, suspension concentrate and flowable solution, is diluted with water to be prepared and adjusted into the suspension or emulsion with a desired concentration, and is applied to crop plants. For the formulations, such as granular and dust formulations, the formulation itself is directly applied to the target crop plants or soil.

Needless to say that the compound alone according to the present invention has sufficient insecticidal and acaricidal activity, however, it can be combined for the use with one or more of various types of other plant protection chemicals, for example, fungicides, insecticides, acaricides and synergists.

Hereunder, representative examples for fungicides, insecticides, acaricides and plant growth regulators those which can be combined to use with the compound according to the present invention will be recited below.

Fungicides:
Captan, Folpet, Thiuram, Ziram, Zineb, Maneb, Mancozeb, Propineb, Polycarbamate, Chlorothalonil, Quintozene, Captafol, Iprodione, Procymidone, Vinclozolin, Fluorimide, Cymoxanil, Mepronil, Flutolanil, Pencycuron, Oxycarboxine, Fosetyl aluminium, Propamocab, Triadimefon, Triadimenol, Propiconazole, Diclobutrazol, Bitertanol, Hexaconazol, Microbutanil, Flusilazole, Etaconazole, Fluotrimazole, Flutriafen, Penconazole, Diniconazole, Cyproconazole, Fenarimol, Triflumizole, Prochloraz, Imazalyl, Pefurazoate, Tridemorph, Fenpropimorph, Triforine, Buthiobate, Pyrifenox, Anilazine, Polyoxins, Metalaxyl, Oxadixyl, Furalaxyl, Isoprothiolane, Probenazole, Pyrrolenitrine, Blastocidin-S, Kasugamycin, Balidamycin, Dihydrostreptomycin sulfate, Benomyl, Carbendazim, Thiophanate methyl, Hymexazol, Basic copper chloride, Basic copper sulfate, Fentin acetate, Triphenyltin hydroxide, Diethofencarb, Metasulfocarb, Quinomethionate, Binapacryl, Lecithin, Sodium hydrogencarbonate, Dithianone, Dinocap, Fenaminosulf, Diclomezine, GuaztineDodine, IBP, Edifenphos, Mepanipyrim, Ferimzone, Trichlamide, Metasulfocarb, Fluazinam, Ethoquinolac, Dimetomorph, Pyroquilon, Tecloftalam, Fthalide, Fenazine oxide, Thiabedazole, Tricyclazole, Vinclozolin, Cymoxanil, Cyclobutanil, Guaztine, Propamnocarb hydrochloride, Oxolinic acid.

Insecticides and Acaricides:
Organophosphorous and carbamate insecticides: Fenthion, Fenitrothion, Diazinon, Chlorpyrifos, ESP, Vamidothion, Fenthoate, Dimethoate, Formothion, Malathion, Trichlorfon, Thiometon, Phosmet, Dichlorvos, Acephate, EPBP, Methyl parathion, Oxadimeton methyl, Ethion, Salithion, Cyanophos, Isoxathione, Pyridafenthion, Phosalone, Methidathion, Sulprofos, Chlorfevinphos, Tetrachlorvinphos, Dimethylvinphos, Propaphos, Isofenphos, Ethyl thiometon, Profenophos, Pyraclofos, Monocrotophos, Azinphos methyl, Aldicarb, Methomyl, Dithiocarb, Carbofuran, Carbosulfan, Benfuracarb, Furathiocarb, Propoxur, BPMC, MTMC, MIPC, carbaryl, Pyrimicarb, Ethiofencarb, Fenoxycarb, cartap, thiocyclam, bensultap, etc.

Pyrethroid insecticides: Permethrin, Cypermethrin, Deltamethrin, Fenvalerate, Fenpropatlrin, Pyrethrin, Allethrin, Tetramethrin, Resmethrin, Dimethrin Propathrin, Fenothrin, Prothrin, Fluvalinate, Cyfluthrin, Cyhalothrin, Flucythrinate, Ethofenprox, Cycloprothrin, Tralomethrin, Silafluofen, Brofenprox, Acrinathrin, etc.

Bezoyl urea and other insecticides: Diflubenzuron, Chlorfluazuron, Hexaflumuron, Triflumuron, Tetrabenzuron, Fulfenoxuron, Flucycloxuron, Buprofezin, Pyriproxyfen, Methoprene, Benzoepin, Diafenthiuron, Imidacloprid, Fipronyl, Micotin sulfate, Rotenone, Metaldehyde, Machine oil, Microbial insecticides such as BT and insect-pathogenic viruses, etc.

NEMATICIDES: Fenamiphos, Fosthiazate, etc.

Acaricides:
Chlorbenzilate, Fenisobromolate, Dicofol, Amitraz, BPPS, Benzomate, Hexythiazox, Fenbutatin oxide, Polynactin, Quinomethionate, CPCBS, Tetradifon, Avermectin, Milbemectin, Clofentezin, Cyhexatin, Pyridaben, Fenpyroxymate, Tebufenpyrad, Pyrimidifen, Fenothiocarb, Dienochlor, etc. Plant Groth Regulators: Gibberellins(e.g., Gibberellin A3, Gibberellin A4, Gibberellin A7). IAA, NAA, etc.

EXAMPLES

The following examples serve to provide further appreciation of the invention but are not meant in any way to restrict the effective scope of the invention. The structures of isolated novel compounds were confirmed by NMR, Mass, and/or other appropriate analysis.

Example 1

2-Amino-5-chloro-4-trifluoromethylthiazole

2-Amino-4-trifluoromethylthiazole (10 g) was dissolved in acetonitrile (80 ml) and N-chlorosuccinimide (8.8 g) was added at room temperature with stirring. The mixture was refluxed for 9 hr and the solvent was removed under reduced pressure. The residue was dissolved in chloroform and washed with cold diluted aqueous sodium hydroxide. The chloroform layer was dried over magnesium sulfate and the solvent was removed under reduced pressure to give crude 2-Amino-5-chloro-4-trifuloromethylthiazole (12 g). It was recrystallized from n-hexane-benzene (1:1 mixture) as colorless needles (6.8 g), m. p. 107–108° C.

Example 2

2-Amino-5-iodo-4-trifuloromethylthiazole

2-Amino-4-trifluoromethylthiazole (10 g) was dissolved in acetonitrile (100 ml) and N-iodosuccinimide (14.7 g) was added at room temperature with stirring. The mixture was refluxed for 6 hr and the solvent was removed under reduced pressure. The residue was dissolved in chloroform and washed with cold diluted aqueous sodium hydroxide. The chloroform layer was dried over magnesium sulfate and the solvent was removed under reduced pressure to give crude 2-Amino-5-iodo-4-trifuloromethylthiazole (16 g). It was recrystallized from n-hexane-benzene (1:1 mixture) as pale orange prisms (10.9 g), m. p. 108–109° C.

Example 3

2-Amino-5-thiocyanato-4-trifuloromethylthiazole

2-Amino-4-trifluoromethylthiazole (10 g), ammonium thiocyanate (13.6 g) was mixed in acetic acid (120 ml) and bromine (9.6 g) in acetic acid (100 ml) was added dropwise at 5–10° C. for 1 hr with stirring. The mixture was further stirred for 1 hr at room temperature. The solvent was removed under reduced pressure and the residue was added ice water then neutralized with aqueous sodium carbonate. The precipitates were filtered off and recrystallized from methanol-water to give 2-Amino-5-thiocyanato-4-trifuloromethylthiazole (9.5 g) as pale green crystals, m. p. 147–150° C.

Example 4

N-(5-Iodo-4-trifluoromethylthiazol-2-yl)-2,6-dichloro-benzamide

2-Amino-5-iodo-4-trifluoromethylthiazole (0.8 g) was dissolved in pyridine (3 ml) and 2,6-dichlorobenzoylchloride (0.6 g) was added at room temperature with stirring. The mixture was stirred for 1 day at room temperature. The mixture was poured into ice water and acidified with aqueous hydrochloric acid then extracted with chloroform. The chloroform layer was dried over magnesium sulfate and the solvent was removed under reduced pressure. The solid thus obtained was recrystallized from methanol to give N-(5-iodo-4-trifluoromethylthiazol-2-yl)-2,6-dichlorobenzamide (0.9 g), m. p. 157–159° C.

Example 5

N-(5-Iodo-4-trifluoromethylthiazol-2-yl)-4-trifluoromethyl-benzamide

2-Amino-5-iodo-4-trifluoromethylthiazole (2.5 g) was dissolved in pyridine (8 ml) and 4-trifluoromethylbenzoylchloride (1.8 g) was added at room temperature with stirring. The mixture was stirred for 1 day at room temperature. The mixture was poured into ice water and acidified with aqueous hydrochloric acid then extracted with chloroform. The chloroform layer was dried over magnesium sulfate and the solvent was removed under reduced pressure. The solid thus obtained was recrystallized from methanol to give N-(5-iodo-4-trifluoromethylthiazol-2-yl)-4-trifluoro-methylbenzamide (2.9 g), m. p. 197–198° C.

Example 6

N-(5-Bromo-4-trifluoromethylthiazol-2-yl)-3,4-dicloro-benzamide

2-Amino-5-bromo-4-trifluoromethylthiazole (1.0 g) was dissolved in pyridine (5 ml) and 3,4-dichlorobenzoylchloride (0.85 g) was added at room temperature with stirring. The mixture was stirred for 5 hr at room temperature. The mixture was poured into ice water and acidified with aqueous hydrochloric acid then extracted with chloroform. The chloroform layer was dried over magnesium sulfate and the solvent was removed under reduced pressure. The solid thus obtained was recrystallized from methanol to give N-(5-bromo-4-trifluoromethylthiazol-2-yl)-3,4-dicloro-benzamide (1.29 g), m. p. 191–192° C.

Example 7

N-(5-Chloro-4-trifluoromethylthiazol-2-yl)-4-chloro-3-nitrobenzamide

2-Amino-5-chloro-4-trifluoromethylthiazole (1.0 g) was dissolved in pyridine (5 ml) and 4-chloro-3-nitrobenzoylchloride (1.1 g) was added at room temperature with stirring. The mixture was stirred for 1 day at room temperature. The mixture was poured into ice water and acidified with aqueous hydrochloric acid then extracted with chloroform. The chloroform layer was dried over magnesium sulfate and the solvent was removed under reduced pressure. The solid thus obtained was recrystallized from methanol to give N-(5-chloro-4-trifluoromethylthiazol-2-yl)-4-chloro-3-nitro-benzamide (0.83 g), m. p. 183–184° C.

Example 8

N-(5-Iodo-4-trifluoromethylthiazol-2-yl)-3,5-bis-trifluoromethylbenzamide

2-Amino-5-iodo-4-trifluoromethylthiazole (1.0 g) was dissolved in pyridine (2 ml) and 3,5-bis-trifluoromethylbenzoylchloride (0.95 g) was added at room temperature with stirring. The mixture was stirred for 6 hr at room temperature. The mixture was poured into ice water and acidified with aqueous hydrochloric acid then extracted with chloroform. The chloroform layer was dried over magnesium sulfate and the solvent was removed under reduced pressure. The solid thus obtained was recrystallized from methanol to give N-(5-iodo-4-trifluoromethylthiazol-2-yl)-3,5-bis-trifluoromethylbenzamide (1.3 g), m. p. 172–173° C.

Example 9

N-(5-Bromo-4-trifluoromethylthiazol-2-yl)thiophene-2-carboxamide

2-Amino-5-iodo-4-trifluoromethylthiazole (1.2 g) was dissolved in pyridine (2 ml) and thiophene-2-carbonyl chloride (0.80 g) was added at room temperature with stirring. The mixture was stirred for 6 hr at room temperature. The mixture was poured into ice water and acidified with aqueous hydrochloric acid then extracted with chloroform The chloroform layer was dried over magnesium sulfate and the solvent was removed under reduced pressure. The solid thus obtained was recrystallized from methanol to give N-(5-iodo-4-trifluoromethylthiazol-2-yl)thiophene-2-carboxamide (1.2 g), m. p. 184–185° C.

Example 10

N-(5-(4-Fluorophenyl)-4-trifluoromethylthiazol-2-yl)-4-trifluoromethylbenzamide N-(5-Iodo-4-trifluoromethylthiazol-2-yl)-4-trifluoromethylbenzamide (0.8 g), powdered sodium hydroxide (0.29 g), tetrakis(triphenylphosphine)-palladium (0) (0.2 g) and 4-fluorophenylboronic acid (0.24 g) were mixed together in tetrahydrofuran (30 ml). The resulting suspension was refluxed for 8 hr with stirring. The solvent was removed under reduced pressure and the residue was mixed with water then extracted with chloroform. The chloroform layer was dried over magnesium chloride and the solvent was removed under reduced pressure. The solid remained was recrystallized from methanol to give N-(5-(4-fluorophenyl)-4-trifluoromethylthiazol-2-yl)-4-trifluoromethylbenzamide as slightly gray needles (0.55 g), m. p. 203–205° C.

Example 11

N-(5-thiocyanato-4-trifluoromethylthiazol-2-yl)-3-trifluoromethylbenzamide

2-Amino-5-thiocyanato-4-trifluoromethylthiazole (0.8 g) was dissolved in pyridine (5 ml) and 3-trifluoromethylbenzoylchloride (0.8 g) was added at room temperature with stirring. The mixture was stirred for one night at room temperature. The mixture was poured into ice water and acidified with aqueous hydrochloric acid then extracted with chloroform. The chloroform layer was dried over magnesium sulfate and the solvent was removed under reduced pressure. The solid thus obtained was recrystallized from carbon tetrachloride to give N-(5-thiocyanato-4-trifluoromethylthiazol-2-yl)-3-trifluoromethylbenzamide (0.8 g), m. p. 167–168° C.

Examples for carrying out the formulations comprising the compound of the present invention will be explained. However, it should be noted that the type and incorporating rate of additives are not limited to those described in the following examples and may be modified over extensive range. Note that the term of "part" in the formulation example described below denotes "part by weight".

Example 12

Wettable Powder Formulation

| A compound of present invention | 40 part |
|---|---|
| Diatomaceous earth | 53 part |
| Higher alcohol sulfate | 4 part |
| Alkylnaphthalenesulfonate | 3 part |

The components given above are mixed and pulverized to fine particles to thereby give a wettable powder formulation for the compound of the present invention with the content of 40% based on the active ingredient.

Example 13

Emulsifiable Concentrate Formulation

| A compound of present invention | 30 part |
|---|---|
| Xylene | 33 part |
| Dimethylformamide | 30 part |
| Polyoxyethylene alkyl allyl ether | 7 part |

The components given above are mixed and prepared to a solution to thereby give an emulsifiable concentrate formulation for the compound of the present invention with the content of 30% based on the active ingredient.

Example 14

Dust Formulation

| A compound of present invention | 10 part |
|---|---|
| Talc | 89 part |
| Polyoxyethylene alkyl allyl ether | 1 part |

The components given above are mixed and pulverized to fine particles to thereby give a dust formulation for the compound of the present invention with the content of 10% based on the active ingredient.

Example 15

Granular Formulation

| A compound of present invention | 5 part |
|---|---|
| Clay | 73 part |
| Bentonite | 20 part |
| Dioctylsulfosuccinate sodium salt | 1 part |
| Sodium phosphate | 1 part |

The components given above are mixed, thoroughly grinded, added with water, then kneaded, and granulated, and further dried to thereby give a granular formulation for the compound of the present invention with the content of 5% based on the active ingredient.

Example 16

Suspension Concentrate Formulation

| A compound of present invention | 10 part |
|---|---|
| Sodium ligninsulfonate | 4 part |
| Sodium dodecylbenzenesulfonate | 1 part |
| Xanthane gum | 0.2 part |
| Water | 84.8 part |

The components given above are mixed and grinded by wet grinding to a particle size of less than 1 μm to thereby give a suspension concentrate for the compound of the present invention with the content of 10% based on the active ingredient.

Example 17

Efficacy Against *Tetranychus urticae* (Tu; Two-spotted Spider Mites

Fifteen adult females were inoculated on a potted Kidney-bean seedling. On the next day, the chemical solution at different concentration was sprayed on the Kidney-bean seedling by a glass nozzle using an air compressor. After air-dried the Kidney-bean pot was maintained in a room kept at 25° C. and 65%RH.

On three days after treatment, the numbers of dead and alive mites were counted and mortality was calculated by Abbott's formula.

Each test was duplicated.

$$\text{mortality} = \frac{\text{Survival rate in untreated plot} - \text{Survival rate in treated plot}}{\text{Survival rate in untreated plot}} \times 100$$

The results show that the following compounds had mortality of 100%: 19, 23, 33, 47, 88.

Example 18

Efficacy Against *Pseudaletia separata* Walker (Ps; Rice Armyworm)

A piece of Maize leaf (ca. 7×1.5 cm) was dipped in the chemical solution at 125 ppm for 30 sec and air-dried. The leaf was placed in a glass petri dish (9 cm diameter) and five second-instar larvae of *Pseudaletia separata* were introduced into the petri dish. Five days after the treatment, the number of survival larvae was counted and the mortality was calculated by Abbott's formula. Each test was duplicated. The results show that the following compounds had mortality of 100%: 1, 7, 13, 14, 19, 20, 23, 33, 35, 44, 45, 47, 59, 81, 88, 89.

Example 19

Efficacy Against *Plutella xylostella* Linne (Px; Diamondback Moth)

The chemical solution at 125 ppm was sprayed on a Cabbage seedling by a glass nozzle using an air compressor. After airdried, a small leaf (ca. 5 cm diameter) was detached from the treated plant and placed in a glass petri dish (ca. 9 cm diameter). Five second-instar larvae of *Plutella xylostella* were introduced into the petri dish. Three days after the treatment, the number of survival larvae was counted and the mortality was calculated by Abbott's formula. Each test was duplicated. The results show that the following compounds had mortality of 100%: 1, 13, 19, 23, 45, 47, 88, 89.

TABLE 1

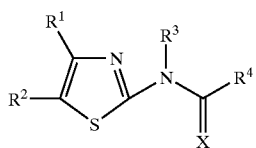

| Compound No. | R¹ | R² | R³ | R⁴ | X | m.p. |
|---|---|---|---|---|---|---|
| 1 | $CF_3$ | I | H | 3-$CF_3$—$C_6H_4$ | O | 171–172 |
| 2 | $CF_3$ | I | H | 2,6-$F_2$—$C_6H_3$ | O | 203–204 |
| 3 | $CF_3$ | Cl | H | 4-Me—$C_6H_4$ | O | 142–143 |
| 4 | $CF_3$ | Cl | Me | 3-Cl—$C_6H_4$ | O | |
| 5 | $CF_3$ | Cl | H | 2,4-$F_2$—$C_6H_3$ | O | |
| 6 | $CF_3$ | Cl | H | 2,4,6-$Me_3$—$C_6H_2$ | O | |
| 7 | $CF_3$ | I | H | 4-t-Bu—$C_6H_4$ | O | 189–190 |
| 8 | $CF_3$ | F | H | 3-$CF_3$—$C_6H_4$ | O | |
| 9 | $CF_3$ | F | H | 4-Cl—$C_6H_4$ | O | |
| 10 | $CF_3$ | Br | H | 2,4-$Cl_2$—$C_6H_3$ | S | |
| 11 | $CF_3$ | I | H | 3,4-$Cl_2$—$C_6H_3$ | S | |
| 12 | $CF_3$ | Cl | H | 2,4-$F_2$—$C_6H_3$ | S | |
| 13 | $CF_3$ | Br | H | 3-$CF_3$—$C_6H_4$ | O | 113–114 |
| 14 | $CF_3$ | Br | H | $C_6H_5$ | O | 155–157 |
| 15 | $CF_3$ | I | H | 3-$CF_3$—$C_6H_4$ | N—OMe | 107–108 |
| 16 | CN | I | H | 3-$CF_3$—$C_6H_4$ | O | |
| 17 | CN | I | H | 3-Cl—$C_6H_4$ | O | |
| 18 | $CF_3$ | I | Me | 3-$CF_3$—$C_6H_4$ | S | |
| 19 | $CF_3$ | Br | H | 3,4-$Cl_2$—$C_6H_3$ | O | 191–192 |
| 20 | $CF_3$ | Br | H | 2,6-$Cl_2$—$C_6H_3$ | O | 154–155 |
| 21 | $C_2F_5$ | I | H | 3-Cl—$C_6H_4$ | O | |
| 22 | $C_2F_5$ | I | H | 3-$CF_3$—$C_6H_4$ | O | |
| 23 | $CF_3$ | Br | H | 4-$CF_3$—$C_6H_4$ | O | 193–194 |
| 24 | $CF_3$ | Cl | H | 4-t-Bu—$C_6H_4$ | S | |
| 25 | $CF_3$ | I | H | 4-OMe—$C_6H_4$ | N—OEt | |
| 26 | $CF_3$ | 4-$CF_3$—$C_6H_4$ | H | 3-$CF_3$—$C_6H_4$ | O | |
| 27 | CN | 4-$C_6H_5$—$C_6H_4$ | H | 3-$CF_3$—$C_6H_4$ | O | |
| 28 | $CF_3$ | Br | H | 2-$CF_3$—$C_6H_4$ | O | |
| 29 | $CF_3$ | Br | H | 3-Cl—$C_6H_4$ | O | |
| 30 | $CF_3$ | Br | H | 3-$OCF_3$—$C_6H_4$ | O | |
| 31 | $CF_3$ | F | H | 2,6-$OMe_2$—$C_6H_3$ | O | |
| 32 | $CF_3$ | SCN | H | 4-Cl—$C_6H_4$ | O | |
| 33 | $CF_3$ | Br | H | 2,4-$F_2$—$C_6H_3$ | O | 143–144 |
| 34 | $CF_3$ | Br | H | 2-thienyl | O | 184–185 |
| 35 | $CF_3$ | I | H | 1-$C_6H_5$-5-$CF_3$-pyrazol-4-yl | O | 144–145 |
| 36 | $C_3F_7$ | I | H | 4-Cl—$C_6H_4$ | O | |
| 37 | $CF_3$ | F | H | 2,4-$Cl_2$—$C_6H_3$ | O | |
| 38 | $CF_3$ | 4-$C_6H_5O$—$C_6H_4$ | H | 4-Me—$C_6H_4$ | O | |
| 39 | $CF_3$ | Cl | Me | 4-Me—$C_6H_4$ | O | 120–121 |
| 40 | $CF_3$ | I | H | 2,4,6-$Cl_3$—$C_6H_2$ | O | |
| 41 | $CF_3$ | I | H | 4-$C_6H_4$—$C_6H_4$ | O | |
| 42 | $CF_3$ | I | H | 4-n-$C_6H_{11}$—$C_6H_4$ | O | |
| 43 | CN | Br | H | 3-Cl—$C_6H_4$ | S | |
| 44 | $CF_3$ | I | H | 2,6-$Cl_2$—$C_6H_3$ | O | 157–159 |
| 45 | $CF_3$ | I | H | 4-$CF_3$—$C_6H_4$ | O | 197–198 |
| 46 | $CF_3$ | Br | H | t-Bu | O | 145–147 |
| 47 | $CF_3$ | Cl | H | 2,4-$Cl_2$—$C_6H_3$ | O | 146–147 |
| 48 | $CF_3$ | Cl | H | n-$C_{17}H_{35}$ | O | 23–24 |
| 49 | $CF_3$ | Cl | H | cyclohexyl | O | |
| 50 | $CF_3$ | I | H | 4-$C_6H_4$—$C_6H_4$ | S | |
| 51 | $CF_3$ | Br | H | 2,4-$Me_2$—$C_6H_3$ | S | |
| 52 | $CF_3$ | Br | H | 4-$C_6H_4O$—$C_6H_4$ | O | |
| 53 | $CF_3$ | Br | H | 4-Cl-2-Me—$C_6H_3$ | O | |
| 54 | $CF_3$ | Br | Me | 2,4-$F_2$—$C_6H_3$ | O | |
| 55 | CN | I | H | 3-$CF_3$—$C_6H_4$ | S | |
| 56 | $CF_3$ | Br | H | 2,6-$(OMe)_2$—$C_6H_3$ | O | |
| 57 | $CF_3$ | Cl | Me | 4-Me-$C_6H_4$ | S | 101–102 |
| 58 | $CF_3$ | Cl | H | 2,6-$Cl_2$—$C_6H_3$ | O | 153–154 |
| 59 | $CF_3$ | Cl | H | $C_6H_5$ | O | 143–144 |
| 60 | $C_3F_7$ | I | H | 3-$CF_3$—$C_6H_4$ | O | |
| 61 | $CF_3$ | I | Me | 3,4-$Cl_2$—$C_6H_3$ | S | |
| 62 | $CF_3$ | Br | H | 3-CN—$C_6H_4$- | O | |
| 63 | $CF_3$ | 3-$C_6H_5$—$C_6H_4$ | H | 3-$CF_3$—$C_6H_4$ | O | |
| 64 | $CF_3$ | I | H | 4-$CO_2Et$—$C_6H_4$ | O | |
| 65 | $CF_3$ | Br | H | 3-F—$C_6H_4$ | O | |
| 66 | $CF_3$ | Br | H | 3,5-$Me_2$—$C_6H_3$ | O | |
| 67 | $CF_3$ | I | H | 3-$CF_3$—$C_6H_4$ | N—O—$CH_2CO_2Et$ | |
| 68 | $CF_3$ | Br | H | 2-Cl-4-CN—$C_6H_3$ | O | |

TABLE 1-continued

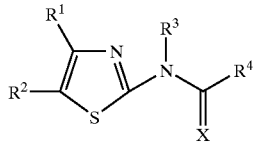

| Compound No. | $R^1$ | $R^2$ | $R^3$ | $R^4$ | X | m.p. |
|---|---|---|---|---|---|---|
| 69 | $CF_3$ | Br | H | 2-Cl-4-OMe—$C_6H_3$ | O | |
| 70 | $CF_3$ | Cl | H | 3-Cl—$C_6H_4$ | S | |
| 71 | $CF_3$ | I | H | 1-naphthyl | S | |
| 72 | $CF_3$ | I | H | 3-Cl—$C_6H_4$ | N—O-allyl | |
| 73 | $CF_3$ | I | H | 4-EtOCO$_2$—$C_6H_4$ | O | |
| 74 | $CF_3$ | Cl | Me | 2,4-Cl$_2$—$C_6H_3$ | O | 95–96 |
| 75 | CN | Br | H | 4-$CF_3$—$C_6H_4$ | S | 220–223 |
| 76 | $CF_3$ | Br | H | 4-$NO_2$—$C_6H_4$ | O | |
| 77 | $CF_3$ | Cl | Me | 3-$CF_3$—$C_6H_4$ | O | 82–83 |
| 78 | $CF_3$ | Br | H | 3-Ac—$C_6H_4$ | O | |
| 79 | $CF_3$ | I | i-Bu | 3-$CF_3$—$C_6H_4$ | O | |
| 80 | $CF_3$ | Cl | H | 4-Cl-3-$NO_2$—$C_6H_3$ | O | 183–184 |
| 81 | $CF_3$ | 4-F—$C_6H_5$ | H | 4-$CF_3$—$C_6H_4$ | O | 203–205 |
| 82 | $CF_3$ | I | H | 2-Cl-4-$CF_3$-thiazol-5-yl | O | 146–147 |
| 83 | $CF_3$ | I | H | 3-$CF_3$—$C_6H_4$ | N—O-propargyl | |
| 84 | $CF_3$ | Br | H | 3,4-OCH$_2$O—$C_6H_3$ | O | |
| 85 | $CF_3$ | Br | H | 4-Me$_2$N—$C_6H_4$ | O | |
| 86 | $CF_3$ | I | H | 3-$OCF_3$—$C_6H_4$ | O | 152–155 |
| 87 | $CF_3$ | I | H | 2-$CF_3$—$C_6H_4$ | O | 137–138 |
| 88 | $CF_3$ | Cl | H | 3-$CF_3$—$C_6H_4$ | O | 115–116 |
| 89 | $CF_3$ | I | H | 3-$CF_3$—$C_6H_4$ | S | 157–158 |
| 90 | $CF_3$ | Br | H | 3-Cl—$C_6H_4$ | O | 133–134 |
| 91 | $CF_3$ | I | H | 1-$CH_3$-3-$CF_3$-pyrazol-4-yl | O | 196–200 |
| 92 | $CF_3$ | I | H | 4-SMe—$C_6H_4$ | O | |
| 93 | $CF_3$ | Cl | H | 2-OMe—$C_6H_4$ | O | 187–188 |
| 94 | $CF_3$ | Cl | H | 3,5-$(CF_3)_2$—$C_6H_3$ | O | 136–137 |
| 95 | $CF_3$ | Cl | H | 3,5-Me$_2$—$C_6H_3$ | O | 158–159 |
| 96 | $CF_3$ | Cl | H | 3,4-Cl$_2$—$C_6H_3$ | O | 198–199 |
| 97 | $CF_3$ | I | H | 4-$SO_2$Me—$C_6H_4$ | O | |
| 98 | $CF_3$ | Br | H | 4-(Cl$_2$C=CH)—$C_6H_4$ | O | |
| 99 | $CF_3$ | Br | H | 4-AcOCH$_2$—$C_6H_4$ | O | |
| 100 | $CF_3$ | I | H | $C_6H_5CH_2$ | O | |
| 101 | CN | Br | H | 4-$CF_3$—$C_6H_4$ | O | 235–236 |
| 102 | $CF_3$ | I | H | 3,5-$(CF_3)_2$—$C_6H_3$ | O | 172–173 |
| 103 | $CF_3$ | I | Ac | 3-$CF_3$—$C_6H_4$ | O | |
| 104 | $CF_3$ | I | $CF_3SO_2$ | 3-$CF_3$—$C_6H_4$ | O | |
| 105 | $CF_3$ | I | MeSO$_2$ | 3-$CF_3$—$C_6H_4$ | O | |
| 106 | $CF_3$ | Cl | Me | 2,4-Cl$_2$—$C_6H_3$ | S | |
| 107 | $CF_3$ | I | $CF_3SO_2$ | 3-Cl—$C_6H_4$ | O | |
| 108 | $CF_3$ | Cl | H | 2,4-F$_2$—$C_6H_3$ | O | 120–121 |
| 109 | $CF_3$ | Cl | H | 4-t-Bu—$C_6H_4$ | O | 173–174 |
| 110 | $C_2F_5$ | I | H | 3,5-$(CF_3)_2$—$C_6H_3$ | O | |
| 111 | $CF_3$ | Cl | Me | 3-$CF_3$—$C_6H_4$ | S | 104–105 |
| 112 | CN | Cl | H | 3-Cl—$C_6H_4$ | O | |
| 113 | $CF_3$ | 3,5-Me$_2$—$C_6H_3$ | H | 3-$CF_3$—$C_6H_4$ | O | |
| 114 | $CF_3$ | I | Et | 3-$CF_3$—$C_6H_4$ | O | |
| 114 | $CF_3$ | I | Ac | 3-$CF_3$—$C_6H_4$ | N—OMe | |
| 115 | $CF_3$ | I | H | 3,5-$(CF_3)_2$—$C_6H_3$ | S | |
| 116 | CN | Br | H | 3-$CF_3$—$C_6H_4$ | S | 215–216 |
| 117 | $CF_3$ | I | H | 2-$CF_3$—$C_6H_4$ | S | |
| 118 | $CF_3$ | F | H | 4-F—$C_6H_4$ | O | |
| 119 | $CF_3$ | Cl | H | 3-pyridinyl | O | 184–185 |
| 120 | CN | I | H | 3,5-$(CF_3)_2$—$C_6H_3$ | O | |
| 121 | CN | Br | H | 3-$CF_3$—$C_6H_4$ | O | 209–210 |
| 122 | $CF_3$ | Cl | H | n-$C_6H_{13}$—$C_6H_4$ | O | |
| 123 | $CF_3$ | Cl | H | 1-naphthyl | O | 141–142 |
| 124 | $CF_3$ | Cl | H | 4-$C_6H_4$—$C_6H_4$ | O | 153–154 |
| 125 | $CF_3$ | Cl | H | 3-$OCF_3$—$C_6H_4$ | O | |
| 126 | $CF_3$ | I | $CF_3SO_2$ | 3,5-$(CF_3)_2$—$C_6H_3$ | O | |
| 127 | $CF_3$ | Cl | H | $C_6H_5CH_2$ | O | 85–86 |
| 128 | $CF_3$ | SCN | H | 2,4-Cl$_2$—$C_6H_3$ | O | |
| 129 | $CF_3$ | Br | H | 3-pyridinyl | O | 182–183 |
| 130 | $CF_3$ | Cl | H | 1-naphthyl | S | |
| 131 | $CF_3$ | SCN | H | 3-$CF_3$—$C_6H_4$ | O | 167–168 |
| 132 | $CF_3$ | 3-$CF_3$—$C_6H_3$ | H | 3-$CF_3$—$C_6H_4$ | O | 250up |
| 133 | $CF_3$ | 4-Cl—$C_6H_4$ | H | 3-$CF_3$—$C_6H_4$ | O | |
| 134 | $CF_3$ | I | H | 4-Cl—$C_6H_4$ | O | |
| 135 | $CF_3$ | I | H | 3-pyridinyl | O | |

TABLE 1-continued

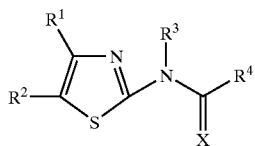

| Compound No. | $R^1$ | $R^2$ | $R^3$ | $R^4$ | X | m.p. |
|---|---|---|---|---|---|---|
| 136 | $CF_3$ | 3-$CF_3$—$C_6H_4$ | H | 3-$CF_3$—$C_6H_4$ | O | |
| 137 | $CF_3$ | I | H | 5-I-4-$CF_3$-thiazol-2-yl | O | |
| 138 | $CF_3$ | I | H | 1-naphthyl | O | |
| 139 | $CF_3$ | SCN | H | 2,6-$F_2$—$C_6H_3$ | O | 125–127 |
| 140 | $CF_3$ | 3-$CF_3$—$C_6H_4$ | H | 3-$CF_3$—$C_6H_4$ | S | 101–103 |
| 141 | $CF_3$ | Cl | H | 3,4-$Cl_2$—$C_6H_3$ | S | 145–146 |
| 142 | $CF_3$ | Br | propargyl | 2,4-$F_2$—$C_6H_3$ | O | 50–52 |

We claim:
1. An insecticide and/or acaricide wherein the insecticide and/or acaricide includes a compound having at least one of a thiazole derivative of formula (1):

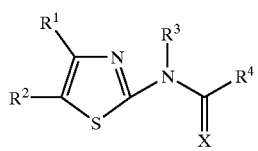

(1)

wherein $R^1$ is cyano or fluoroalkyl (especially $C_1$–$C_4$ fluoroalkyl), $R^2$ is halogen, $R^3$ is H, $C_1$–$C_6$ alkyl, $SO_2R^5$ or $C(O)R^6$, $R^4$ and $R^6$ are, independently, phenyl, being optionally substituted by one or more of halogen, cyano, alkyl, haloalkyl (excluding 3,5-bis-trifluoromethyl), alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is O, S, $NR^7$, $R^7$ is alkyl (especially $C_1$–$C_6$ alkyl), cycloalkyl (especially $C_3$–$C_6$ cycloalkyl), alkoxy (especially $C_1$–$C_6$ alkoxy), alkenylalkyloxy (especially ($C_2$–$C_6$)alkenyl($C_1$–$C_6$)alkyloxy), alkynylalkyloxy (especially ($C_2$–$C_6$)alkynyl($C_1$–$C_6$) alkyloxy), alkoxycarbonylalkyloxy.

2. An agrochemical composition comprising an insecticidally or acaricidally effective amount of a compound having at least one of a thiazole derivative of formula (1)

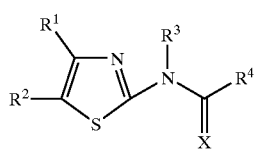

(1)

wherein $R^1$ is cyano or fluoroalkyl (especially $C_1$–$C_4$ fluoroalkyl), $R^2$ is halogen, $R^3$ is H, $C_1$–$C_6$ alkyl, $SO_2R^5$ or $C(O)R^6$, $R^4$ and $R^6$ are, independently, phenyl, being optionally substituted by one or more of halogen, cyano, alkyl, haloalkyl (excluding 3,5-bis-trifluoromethyl), alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is O, S, $NR^7$, $R^7$ is alkyl (especially $C_1$–$C_6$ alkyl), cycloalkyl (especially $C_3$–$C_6$ cycloalkyl), alkoxy (especially $C_1$–$C_6$ alkoxy), alkenylalkyloxy (especially ($C_2$–$C_6$)alkenyl($C_1$–$C_6$) alkyloxy), alkynylalkyloxy (especially ($C_2$–$C_6$)alkynyl ($C_1$–$C_6$)alkyloxy), alkoxycarbonylalkyloxy; and
a carrier or diluent to combat and control insect pests at a locus.

3. A thiazole derivative of formula (1):

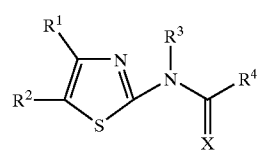

(1)

wherein $R^1$ is cyano or fluoroalkyl (especially $C_1$–$C_4$ fluoroalkyl), $R^2$ is halogen, $R^3$ is H, $C_1$–$C_6$ alkyl, $SO_2R^5$ or $C(O)R^6$, $R^4$ and $R^6$ are, independently, phenyl, being optionally substituted by one or more of halogen, cyano, alkyl, haloalkyl (excluding 3,5-bis-trifluoromethyl), alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is O, S, $NR^7$, $R^7$ is alkyl (especially $C_1$–$C_6$ alkyl), cycloalkyl (especially $C_3$–$C_6$ cycloalkyl), alkoxy (especially $C_1$–$C_6$ alkoxy), alkenylalkyloxy (especially ($C_2$–$C_6$)alkenyl($C_1$–$C_6$) alkyloxy), alkynylalkyloxy (especially ($C_2$–$C_6$)alkynyl ($C_1$–$C_6$)alkyloxy), alkoxycarbonylalkyloxy.

4. An insecticidal or acaricidal composition comprising a thiazole derivative of formula (1):

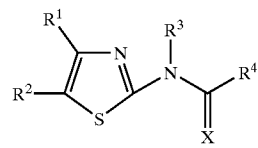

(1)

wherein $R^1$ is cyano or fluoroalkyl (especially $C_1$–$C_4$ fluoroalkyl), $R^2$ is halogen, $R^3$ is H, $C_1$–$C_6$ alkyl, $SO_2R^5$ or $C(O)R^6$, $R^4$ and $R^6$ are, independently, phenyl, being optionally substituted by one or more of halogen, cyano, alkyl, haloalkyl (excluding 3,5-bis-trifluoromethyl), alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is O, S, $NR^7$, $R^7$ is alkyl (especially $C_1$–$C_6$ alkyl), cycloalkyl (especially $C_3$–$C_6$ cycloalkyl), alkoxy (especially $C_1$–$C_6$ alkoxy), alkenylalkyloxy (especially ($C_2$–$C_6$)alkenyl($C_1$–$C_6$)alkyloxy), alkynylalkyloxy (especially ($C_1$–$C_6$)alkynyl($C_1$–$C_6$)alkyloxy), alkoxycarbonylalkyloxy.

5. A process for preparing a compound of formula (1)

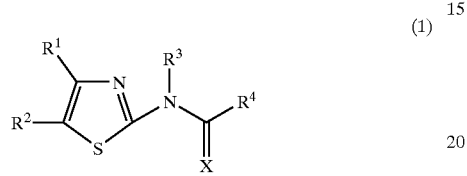

(1)

wherein $R^1$ is cyano or fluoroalkyl (especially $C_1$–$C_4$ fluoroalkyl), $R^2$ is halogen, $R^3$ is H, $C_1$–$C_6$ alkyl, $SO_2R^1$ or $C(O)R^6$, $R^4$ and $R^6$ are, independently, phenyl, being optionally substituted by one or more of halogen, cyano, alkyl, haloalkyl (excluding 3,5-bis-trifluoromethyl), alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is O, by reacting a compound of formula (2)

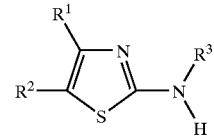

(2)

with a $R^4C(O)Cl$ in the presence of an organic base or an inorganic base.

6. A process for preparing a compound of formula (1)

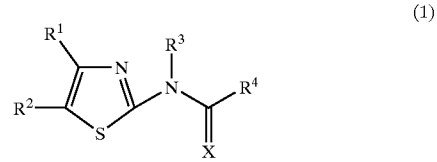

(1)

wherein $R^1$ is cyano or fluoroalkyl (especially $C_1$–$C_4$ fluoroalkyl), $R^2$ is halogen, $R^3$ is H, $C_1$–$C_6$ alkyl, $SO_2R^5$ or $C(O)R^6$, $R^4$ and $R^6$ are, independently, phenyl, being optionally substituted by one or more of halogen, cyano, alkyl, haloalkyl (excluding 3,5-bis-trifluoromethyl), alkoxy, nitro, alkoxycarbonyl, alkylcarbonyloxy, alkylcarbonyl, amino, alkylamino, haloalkoxy, alkylthio, or alkylsulfonyl), $R^5$ is alkyl (especially $C_1$–$C_6$ alkyl), haloalkyl (especially $C_1$–$C_6$ haloalkyl), X is S, by reacting a compound of formula (1) wherein X is O with phosphorous pentasulfide in a high boiling point solvent selected from the group consisting of pyridine, picoline, lutidine, xylene and sulfolane.

\* \* \* \* \*

UNITED STATES PATENT AND TRADEMARK OFFICE
CERTIFICATE OF CORRECTION

PATENT NO. : 6,737,382 B1
DATED : May 18, 2004
INVENTOR(S) : Isao Iwataki et al.

It is certified that error appears in the above-identified patent and that said Letters Patent is hereby corrected as shown below:

<u>Title page,</u>
Item [75], Inventors, replace city of fourth inventor with -- Cordoba, AR --.
Item [56], References Cited, FOREIGN PATENT DOCUMENTS, replace
"JP 1019527 A * 7/1998" with -- JP 1019572 A * 7/1998 --.
OTHER PUBLICATIONS, replace "CA Registry No. 256414-60-0" with -- CA Registry No. 256414-65-0 --.

<u>Column 11,</u>
Table 1, Compound No. 22, under heading m.p. replace "__" with -- 141-143 --.
Table 1, Compound No. 60, under heading m.p. replace "__" with -- 96-98 --.

Signed and Sealed this

Twenty-third Day of November, 2004

JON W. DUDAS
*Director of the United States Patent and Trademark Office*